United States Patent [19]

Granados et al.

[11] Patent Number: 5,591,598
[45] Date of Patent: Jan. 7, 1997

[54] METHOD FOR QUANTITATING HYDRAZIDE GROUPS

[75] Inventors: Edward N. Granados, Vernon Hills; Daniel F. Heiman, Libertyville, both of Ill.; Herbert S. Chow, San Carlos, Calif.; Maria L. Thaler, Waukegan, Ill.

[73] Assignee: Abbott Laboratories, Abbott Park, Ill.

[21] Appl. No.: 391,876

[22] Filed: Feb. 22, 1995

Related U.S. Application Data

[62] Division of Ser. No. 113,145, Aug. 27, 1993, abandoned.

[51] Int. Cl.$^6$ .............................. C12Q 1/02; C12Q 1/24
[52] U.S. Cl. .................... 435/29; 435/4; 435/30
[58] Field of Search .................... 435/4, 29, 30

[56] References Cited

U.S. PATENT DOCUMENTS

| | | | |
|---|---|---|---|
| 4,421,896 | 12/1983 | Dorman | 525/54.1 |
| 5,329,028 | 7/1994 | Ashkenazi | 548/548 |
| 5,349,066 | 9/1994 | Kaneko | 546/294 |

OTHER PUBLICATIONS

Muresan, V., A Hemagglutination Test for Binding of Hydrazide Derivatized Cytochemical Markers, Acta Histochem 79 193–98 (1986).

Traore, F., Determination of Picomole Amounts of Carbonyls as Luminarin Hydrazones by High Performance Liquid Chromatography with Fluorescence Detection, Chromatographia vol. 36 96–104 (1993).

In Vitro Attachment of Mono–and Oligosaccharides to Surface Clycoconjugates of Intact Cells, Tolvanen, M., et al. *The Journal of Biological Chemistry* vol. 261, No. 20 15 Jul. 1986 pp. 9546–9451.

Primary Examiner—Ralph Gitomer
Attorney, Agent, or Firm—Cheryl L. Becker

[57] ABSTRACT

A method is provided for the preparation of semisolid particles or cells that have been chemically derivatized resulting in hydrazide functionalities covalently incorporated onto cell surface membrane molecules of the semisolid particles or cells, as well as a method for determining the levels of hydrazide groups on the particles or cells. The method involves the preparation and analysis of red blood cells chemically derivatized in such a manner that hydrazide functionalities have been covalently incorporated onto the cell membrane molecules, the preparation of hydrazine derivatized cells and the use of the novel cells in agglutination reactions to promote the attachment of antigens and antibodies to the hydrazine derivatized cells without loss of antibody activity or the blocking of the epitope of interest.

2 Claims, 6 Drawing Sheets

METHOD FOR QUANTITATING HYDRAZIDE GROUPS

This is a division of U.S. patent application Ser. No. 08/113,145 filed Aug. 27, 1993, now abandoned.

FIELD OF THE INVENTION

The present invention relates to the preparation and analysis of cells that have been chemically derivatized in such a manner that hydrazide functionalities have been covalently incorporated onto the cell surface molecules. In yet another aspect the invention relates to a methodology for determining the levels of hydrazide groups on solid or semisolid particles or cells.

BACKGROUND OF THE INVENTION

Historically, cells such as erythrocytes and their derivatives have been utilized in diagnostic tests, such as hemagglutination, for many years. British Patent 1244 344 and also U.S. Pat. Nos. 3,714,345 and 3,715,427 to Hirata disclose methods for the preparation of erythrocytes derivatized with pyruvic aldehyde and formaldehyde for use in hemagglutination reactions. Human type A erythrocytes could be coated with antigens such as bovine serum albumin, bacteriophages and gamma-globulins, and used in agglutination reactions. However, the coating process does not control the orientation of coupling of the antigen.

Hydrazine-derivatized materials such as latex particles and chromatography resins, have been coupled to antigens and antibodies. U.S. Pat. No. 4,421,896 to Linneaus C. Dorman describes the preparation of hydrazine-derivatized latex particles for use in latex particle agglutination reactions. Hydrazinolysis of amide groups yielded carboxylic hydrazide groups after about 7 to 8 hours at a temperature of 50 to about 80 degrees C. However, such conditions are much too rigorous for cellular membranes. Additionally, cellular membranes are not typically composed of mostly carboxylic amide groups.

Methods for immobilization of antibodies to solid supports are also known. For example, antibodies can be bound to solid supports by covalent bonds between aldehydes generated on the carbohydrate side chains of the antibody and hydrazide groups on the solid support. The hydrazide affinity supports the binding of immunoglobulins from a variety of species and the immobilized antibodies retain more of their biological activity when compared to similar pore-size supports employing protein non-site directed immobilization chemistry.

Jonathan M. Gershoni et al., in *Analytical Biochemistry* 146:59–63 (1985) disclosed the preparation of adipic dihydrazide derivatized enzymes. Gershoni et al. did not apply this method to cellular membranes, which are much more sensitive to reaction conditions and reagents than proteins in solution.

In view of the foregoing limitations of prior art, it is an object of the present invention to provide a methodology for the preparation and quantitation of semisolid particles or cells that have been chemically derivatized, resulting in hydrazide functionalities covalently incorporated onto the surface molecules of the semisolid particles or cells, as well as a method for determining the levels of hydrazide groups that are on particles or cells.

Another object of the present invention is to prepare derivatized cells useful in agglutination reactions, permitting the controlled attachment of antigens and antibodies to the cells. Hydrazine derivatized cells permit such controlled attachments. Yet another object of the invention is to produce hydrazine derivatized cells under conditions which maintain the integrity of the cellular membrane.

A further object of this invention is to attach antigens and antibodies to hydrazine derivatized cells without loss of the antibody activity or the blocking of the antigen epitope of interest.

An additional object of the invention is to achieve optimal antibody coupling by incorporation onto stabilized red blood cells of optimum levels of hydrazide functionalities.

SUMMARY OF THE INVENTION

The foregoing objects and related advantages thereof are obtained by the present invention in providing for the preparation and use of hydrazine derivatized cells. The invention involves the preparation and analysis of, for example, red blood cells that have been chemically derivatized in such a manner that hydrazide functionalities have been covalently incorporated into their surface molecules. The preparation of hydrazine derivatized cells and their use in agglutination reactions enable preparation of a chemically activated red blood cell to which oxidized antibodies (glycoproteins) can subsequently be covalently attached through their carbohydrate residues. The hydrazine derivatized cells are produced under conditions that maintain the integrity of the cellular membrane while promoting the attachment of antigens and antibodies to the hydrazine derivatized cells without loss of the antibody activity or the blocking of the antigen epitope of interest. The hydrazide formation on a semisolid, for example, red blood cells in an aqueous media, enables mild and stable coupling of antibodies on the red blood cells. The inventive methodology provides for determining the levels of hydrazide groups that are on solid or semi-solid particles or cells inclusive of red blood cells.

The present invention also provides a novel technique for detecting human leukocyte antigen (HLA) alloantibodies. HLA antigens that have been extracted from transformed lymphocytes are immobilized onto fixed red blood cells through a monoclonal antibody framework (MoAb). The HLA antigens are then detected by mixing test sera with the HLA sensitized red blood cells in an agglutination tray. After a suitable incubation period, agglutinated positives are visually differentiated from the negatives.

The technology of the invention provides for a front line screening methodology for detecting the presence of alloantibodies in multiparous serum samples. The specificities of the positive sera are later determined using complement dependent cytotoxicity (CDC). The methodology according to the invention provides for allosera detection by agglutination of HLA sensitized red blood cells.

The utilization of the assay described herein for the front end screening of multiparous sera provides a number of advantages. These advantages include a constant source of antigens from lymphoblast as grown in culture, an assay that does not require complement, reagents that are reasonably stable, an assay configuration and format that is amenable to automation and the potential for eliminating false positives caused by auto antibodies.

BRIEF DESCRIPTION OF THE DRAWINGS

The novel features and advantages of the present invention are set forth in the appended claims, which are preceded by a detailed description of embodiments in accordance with the invention, with reference to the following drawings.

DETAILED DESCRIPTION OF THE INVENTION

Definitions

Figure 1:
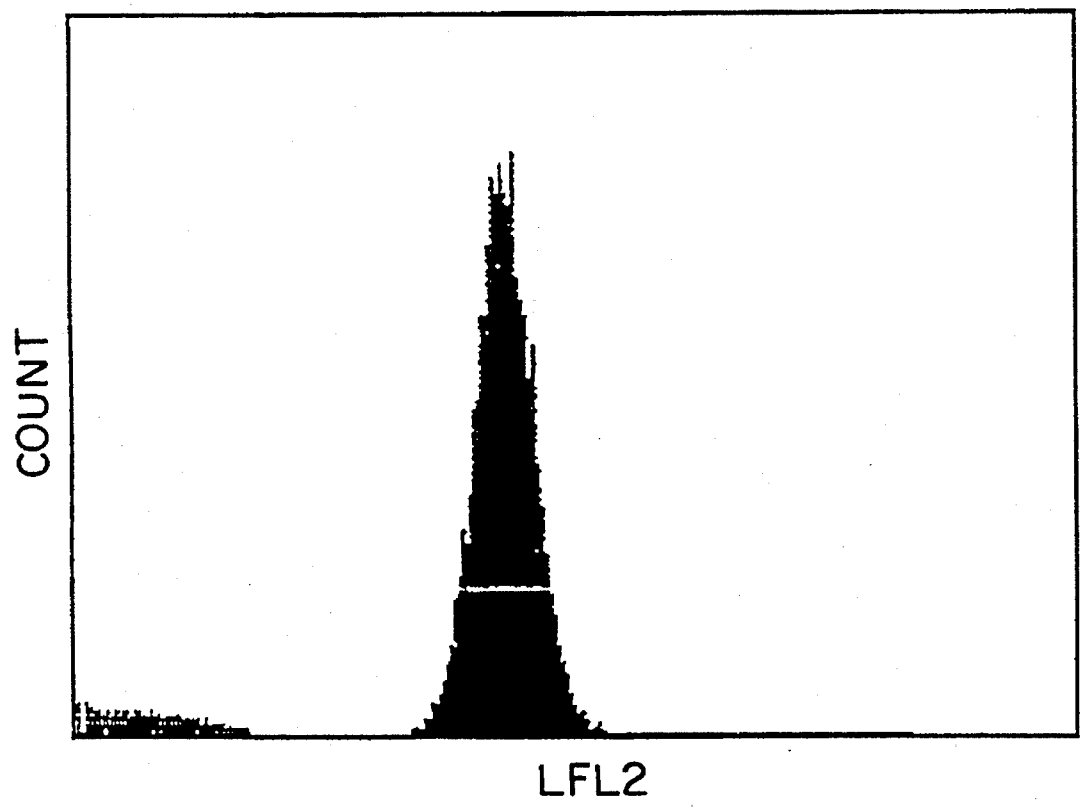
FIG. 1 shows a graph of a log fluorescence shift obtained as a result of the activation of duracytes with hydrazine; the peak on the left is for duracyte, while the peak on the right is for a hydrazine derivatized duracyte (hydracyte)

The following abbreviation definitions are applicable to the present invention and utilized throughout this specification:

Abbreviation: HLA, human leukocyte antigen; HAMA, human anti-mouse antibodies; ELISA, enzyme linked immunoassay; EDAC, 1-ethyl-3-(3-dimethylaminopropyl-)carbodiimide hydrochloride; MES, (2-[N-Morpholino] ethanesulfonic acid); PBS, phosphate buffered saline; DMF, Dimethylformamide; TBL, thiobutyrolactone; OD, optical density (light absorbance) at the specified wavelength; EDTA, ethylenediaminetetraacetic acid; B2M, beta-2-microglobulin; PE, phycoerythrin; FL, fluorescence; LFL, Log fluorescence; CDC, complement dependent cytotoxicity; EBV, Epstein-Bar virus; MoAb, Monoclonal antibody; CYNAP, cytotoxicity negative adsorption positive; PRA, panel reactive antibody.

The invention enables the controlled coupling of receptors or substrates to a cell membrane. The cell surface is derivatized with hydrazine, under mild conditions to avoid destruction of the membrane, to yield hydrazide groups on the cell surface. The receptor or substrate of interest is derivatized with an aldehyde group at a location such that the binding site or epitope remains available to its binding partner after coupling to a cell membrane. The coupling of the receptor or substrate to the cell surface can then be accomplished by reaction of the aldehyde group on the receptor or substrate and the hydrazide on the cell surface.

The invention can be utilized with living, dead or dormant cells, such as erythrocytes, duracytes or bacteria and the like. Stabilized cells, such as stabilized red blood cells (for example, Duracytes, as disclosed in U.S. Pat. Nos. 3,714,345 and 3,715,427, assigned to Abbott Laboratories), and those prepared according to the methodology described in British Patent 1 244 344, are most suitable.

Hydrazide groups can be formed on a cell surface by reacting carboxylic acid groups located on the surface of cellular membranes with hydrazine in the presence of a water soluble activating agent, such as EDAC. The reaction can be performed by simultaneous addition of the reagents. After the reaction is complete, the approximate number of available hydrazides on a cell can be determined. The hydrazide groups are reacted with thiobutyrolactone to form a thiol derivative. The quantity of thiols present can be determined with a thiol detection reagent, such as Ellmans Reagent [5,5'-dithio-bis(2-nitrobenzoic acid)]. The intensity of the color developed in the detection reagent reaction can be correlated to the quantity of thiols present on the cell membrane, and thereby the quantity of hydrazide groups.

Proteins can be derivatized with aldehyde groups through the use of a variety of well known reagents and methods. Preferably, a carbohydrate group located on the protein, such as glucose, is oxidized with an oxidizing agent such as sodium periodate or the like, to a dialdehyde derivative. Other aldehyde forming reactions are well known to those skilled in the art and could easily be adapted for this use without undue experimentation.

This invention is particularly useful for preparation of cells coupled to antibodies. The preferred cell is a duracyte (red blood cell) which is stable and readily detectable. The duracyte is reacted with hydrazine and EDAC to form a hydracyte. The carbohydrate groups on the Fc portion of the antibody can be oxidized to aldehydes with sodium periodate and the like, and the hydracyte can then be coupled to the aldehyde groups by reacting the hydracyte and the derivatized antibodies. The antibody-coupled hydracytes are then used in agglutination reactions to detect the presence or quantity of antigen present in a sample.

The antibody-coupled hydracytes can also be used to couple an antigen to the cell. An antibody specific to a particular epitope on an antigen is coupled to the hydracytes and when this antibody-hydracyte is exposed to the antigen, the antigen binds to the antibody. Thus, the cell is coupled to the antigen through the selected epitope. The presence or quantity in a sample of an anti-antigen antibody to a secondary epitope on the antigen can be determined from the resulting agglutination upon exposure of the sample to the antigen coupled cell. A similar result can be obtained using antigen coupled cells obtained through direct coupling of the antigen to the hydracyte.

Other methods of detecting the presence or quantity of an antibody-antigen complex are well known and equally applicable. For example, homogeneous or heterogeneous immunoassays utilizing antibodies or antigens labeled with enzymes, such as alkaline phosphatase, horseradish peroxidase and the like, and fluorescent compounds, such as fluorescein and the like, can detect antibody-antigen complexes. One skilled in the art could readily adapt these methods of detection to the principles of the present invention without undue experimentation.

The following discussion of materials and methods inclusive of examples are illustrative of the invention and are in no way to be interpreted as limiting the scope of the invention as defined in the claims. It will be appreciated that one skilled in the art can conceive of many other methods of use in which the present inventive concepts can be applied.

MATERIALS AND METHODS

Antibody Reagents

Rabbit anti-B2M-PE, goat anti-mouse and goat anti-mouse-PE were obtained from Sigma Chemical Co. (St. Louis, Mo.)

Serum Reagents

Human anti-OKT3 sera were purchased from the University of Cincinnati (Cincinnati, Ohio). Human anti-HLA allosera, whose PRA and specificities had been determined using the standard no-wash NIH CDC methodology, and human normal sera samples were purchased from the University Hospital of Leiden, Netherlands.

Stabilized Sheep Erythrocytes

Stabilized sheep erythrocytes (Duracytes) were prepared from sheep blood using the methodology described in U.S. Pat. No. 3,714,345, hereby incorporated by reference. Initially, duracytes were prepared from the bleeds of single animals; subsequently, pools of blood obtained from 14–20 animals were used.

EXAMPLE 1

Hydrazine Duracytes (Hydracytes)

Hydrazine derivatized duracytes were prepared using a Radiometer pH stat (ABU 91 AutoBurette) to maintain the reaction pH. Thirty-seven mL of a 13.3% solution of duracytes in 0.01M potassium pyrophosphate (pH 6.0) were added to a 125 mL Radiometer reaction vessel. This suspension was stirred using a small stir bar with the stir rate of the Radiometer stirrer set at "3". Seven and one-half mL of a 50% hydrazine monohydrochloride aqueous solution (pH 6.0) were added to the suspension, so that the final hydrazine solution concentration was about seven and one-half percent by weight. The pH was then adjusted manually to 4.8 with 1.2M hydrochloric acid. Five mL of an EDAC solution (0.2 mg/mL in 50 mM MES, pH 6.0) were added to the suspension. The pH of the reaction was maintained at 5.0 by the automated addition of 1.0M potassium pyrophosphate. After approximately 20 hours, the reaction was terminated by centrifugation of the reaction mixture. The hydrazine derivatized duracytes (hydracytes) were then washed several times with PBS. A final 10% suspension of cells was stored at 4° C. in PBS containing 0.1% sodium azide.

In the foregoing example water soluble EDAC was used, however, other water soluble derivatives of EDAC can be used as well as water soluble carbodiimides, such as, for example, 1-cylohexyl-3-(2-morpholinoethyl)carbodiimide metho-p-toluenesulfonate.

EXAMPLE 2

Hydrazine Quantitation

The levels of hydrazide generated on the stabilized erythrocytes were determined in the following way. Two hundred uL of each hydracyte suspension were added to each of three 2.0 mL microfuge tubes and two hundred uL of underivitized duracyte (controls) were added to a second set of 2.0 mL microfuge tubes. Eight hundred uL of saline was added to each tube. The erythrocytes were then vortexed and centrifuged using a bench top centrifuge. Following centrifugation, the supernate was carefully removed. The erythrocytes were then washed three more times with 1 mL of saline. After the last centrifugation step 400 uL of 0.5M potassium pyrophosphate (pH 5.0) were added to the erythrocyte pellet and the erythrocytes were resuspended by vortexing fifty uL of DMF:TBL (5:2) and the solution was added to each tube. The tubes were vortexed and rotated for five hours (room temperature) on a Labquake rotator. After five hours, 800 uL of saline was added to each tube. The cells were then centrifuged and washed five times with 1 mL of saline. After the last wash, 200 uL of Ellmans reagent (4 mg/mL in 0.1M sodium phosphate, pH 8.0) was added to each erythrocyte pellet (approximately 200 uL). The erythrocytes were vortexed to completely resuspend the cells. After two minutes, the erythrocytes were centrifuged. One hundred uL of each supernate were diluted with 1.9 mL of saline. Absorbance readings were then made at 405 nm. The levels of hydrazide formation were obtained by subtracting the control (duracyte) reading from the hydracyte reading and using a molar extinction coefficient of $1.36 \times 10^4$/cm-M. Since the number of erythrocytes in the pellet is approximately $2.9 \times 10^5$, an $OD_{405}$ of 0.3 (typical value) would translate to $1.87 \times 10^{11}$ hydrazides per erythrocyte.

Flow cytometry was used to follow the activation process. To do this, 10 uL of the reaction was removed from the reaction vessel at various times, and mixed with 1.0 mL of PBS. The fluorescence of the diluted sample was measured on an Epics Profile II Flow Cytometer (Coulter Corp., Hialeah, Fla.). Prior to measurement, standard alignment and fluorescence checks were performed. The data were first collected in a two parameter histogram of size (FS) vs granularity (SS). Bitmaps were drawn around the major density. Histograms of log orange fluorescence (LFL2) vs cell number and orange fluorescence (FL2) vs cell number were generated from the date obtained for the cells in the bitmap. For analysis approximately 10,000 cells were collected in the bitmaps.

EXAMPLE 3

Antibody Isolation

Hybridoma W6/32, obtained from the American Type Culture Collection (Rockville, Md.), was grown in hollow fiber devices using standard procedures. The W6/32 monoclonal antibody was isolated from the hollow fiber fluid by performing a 50% saturated ammonium sulfate cut. The antibody was then dialyzed extensively against PBS followed by 0.1M sodium acetate, 0.15M NaCl, pH 5.0. The antibody solution was then centrifuged for 1 hour at 35,000 rpm at 10° C. in a Beckman L7-65 ultracentrifuge (Ti-45 rotor) for one hour to remove high molecular weight aggregates. The protein concentration was then determined using an absorption coefficient of 1.4 for a 1 mg/mL solution when measuring at 280 nm. In order to ensure that the absorbance measurement was not influenced by light scattering of aggregates, a scan between 320 nm and 245 nm was run. If the OD320/OD280 was greater than 0.1 and/or the $OD_{280}$/$OD_{250}$ was less than 1.9, the protein solution was reclarified by ultracentrifugation.

EXAMPLE 4

Antibody Oxidation

The antibody was oxidized with sodium metaperiodate following the procedure described by Hoffman and O'Shanessy (*Journal of Immunological Methods*, 112, 113 (1988), hereby incorporated by reference. For each mL of protein to be oxidized (at 6.0 mg/mL) 50 uL of a sodium metaperiodate solution (100 mg/mL in H20) were added. The reaction vessel was inverted by hand to mix the reagents and then rotated gently for 2 hours between 4° C. and 8° C. After 2 hours, the reaction was quenched by the addition of a glycerol solution (100 uL of a 0.2M solution in H20 per mL of protein solution). The quenched solution was then dialyzed against the acetate-NaCl buffer and reclarified by ultracentrifugation. The extent of oxidation was determined using the method described by Ahn, et al., "Use of Fluorescein Hydrazide and Fluorescein Thiosemicarbazide Reagents for the Fluorometric Determination of Protein Carbonyl Groups and for the Detection of Oxidized Protein on Polyacrylamide Gels", *Anal. Biochem.*, 161, 245 (1987), hereby incorporated by reference. Under these oxidation conditions, approximately 3.6 aldehydes were generated for each antibody molecule.

EXAMPLE 5

W6/32-Hydracytes

Oxidized W6/32 was coupled to hydracytes in the following manner. Two mL of a 10% suspension of hydracytes were placed in a 2.0 mL Sarstedt plastic vial. The suspension was centrifuged and the supernate was removed leaving behind 200 uL of packed hydracytes. Eight hundred uL of oxidized antibody was added to the vial. The packed hydracytes were resuspended in the solution and then the reaction was rotated for 24 hours at room temperature using a Labquake Shaker (Labindustries, Inc.). After 24 hours, the reaction mixture was centrifuged and the supernate was removed. The cells were washed twice with PBS, coated with a 1.0% solution of human serum albumin (pH 8) for 90 minutes at room temperature, rewashed with PBS, and then resuspended to the original volume with PBS-azide. The suspensions were stored at 4° C.

Transformed Lymphoblasts

Blood from selected human donors was drawn at the Blood Center of Southeastern Wisconsin (Milwaukee, Wis.) and shipped to the Coriell Institute (Camden, N.J.) where lymphocytes were isolated and B lymphocytes transformed with EBV. Transformed lymphoblasts were returned to Abbott Laboratories where they were grown in liquid suspension culture. The HLA Class I phenotypes of the lymphocytes were obtained at the Blood Center of Southeastern Wisconsin, before and after transformation, using the NIH microlymphocytotoxicity assay.

EXAMPLE 6

Solubilized HLA

HLA was solubilized, using minor variations of the procedures described by Parham in "Purification of Immunologically Active HLA-A and -B Antigens by a Series of Monoclonal Antibody Columns", *J. Biochem.*, 54, 8709 (1979), hereby incorporated by reference, from transformed cells that were grown in culture. Briefly, for each gram of frozen cell pellet 1.34 mL of 10 mM Tris, 0.025 sodium azide, pH 8.0 were added, followed by 0.71 mL of a 20% Brij solution (13.3% Brij 99, 6.7% Brij 97) and 0.16 mL of a 20 mM iodoacetamide solution (in 10 mM Tris-azide, pH 8.0). The resulting suspension was stirred for 2 hours at 2° to 8° C., transferred to 2.0 mL microfuge tubes and then centrifuged for 5 minutes on a bench top centrifuge. The clear supernate was removed and transferred to a new centrifuge tube. Care was taken to avoid transferring any floating material. The sample was centrifuged and supernate was then transferred to new tubes and stored frozen at −70° C.

EXAMPLE 7

HLA-Hydracytes

Two mL of a 10% suspension of W6/32-hydracytes were added to a 2.0 mL Sarstedt vial. After centrifugation, the supernate was removed and 1.0 mL of a 1:3 solution of solubilized HLA (10 to 30 ug/mL) in PBS-azide were added to the packed hydracytes. The cells were resuspended and rotated for one hour at room temperature, as previously described. After one hour, the cells were centrifuged, washed several times with PBS, and resuspended to the original volume with PBS-azide. The cells, in capped vials, were then "cured" by rotating for 72 hours at 37° C. After curing, the cells were transferred, without washing, to storage at 2° to 8° C.

EXAMPLE 8

Serum Adsorption

In order to eliminate interferences due to human antibodies that cross-react with mouse immunoglobulins, all human sera samples were first adsorbed with a combination solid-liquid phase reagent. To accomplish this, 2.0 mL of a 10% suspension of W6/32-hydracytes were added to a 2.0 mL Sarstedt plastic vial which was then centrifuged. The supernate was then removed and discarded. One mL of sera was then added to the remaining 200 uL cell pellet. A nonspecific antibody of the same isotype as W6/32 (IgG2A) was also added (200 uL of a 6 mg/mL buffer K solution) as well as bovine serum albumin (100 uL of a 40 mg/mL buffer K solution), 0.05M sodium phosphate, 0.75 sodium chloride and 0.02M EDTA at pH 7.6. The packed cells were then resuspended in the serum diluent mixture, which was then rotated for 1 hour on a Labquake rotator. The tubes were then centrifuged and the adsorbed, diluted sera was removed for agglutination analysis.

EXAMPLE 9

HLA Quantitation

HLA extracted from lymphoblasts was quantitated using a standard sandwich ELISA, employing rabbit anti-human B2M as the capture antibody, W6/32 as the specific antibody and goat anti-mouse alkaline phosphatase as the secondary labeling antibody. Initially, results were reported as relative units. Later, the commercially available Sangstat sHLA ELISA kit (Menlo Park, Calif.) was used to determine actual values. For most of the cells extracted, between 40 and 120 ug of HLA were obtained per mL of extraction solution.

EXAMPLE 10

Flow Cytometry Analysis

W6/32-hydracytes and HLA-hydracytes were routinely analyzed by flow cytometry using PE labeled goat anti-mouse and PE rabbit anti-human $B_2M$. To accomplish this, 25 uL of W6/32-hydracytes (10%) were diluted with 100 uL of PBS in 200 uL serum tubes (in duplicate). The tubes were briefly centrifuged and supernate was removed. At this point, 50 uL of a ⅕ dilution of anti-mouse-PE, or a ¹⁄₄₀ dilution of anti-B2M-PE, were added to the cells. Dilutions of the anti-mouse-PE or anti-B2M-PE, were made using buffer that contained approximately 20% goat serum and 10% bovine serum and 0.02% Tween 20. Diluent only was added to control tubes. Extract from the Daudi cell line was also used as a control. Cells were resuspended by vortexing and rotated for 2 hours at room temperature. After 2 hours, the cells were washed 2 times with 100 uL of PBS. For flow analysis 10 uL of the cell suspensions were transferred to tubes containing 1.0 mL of PBS. These diluted cells were then analyzed on a Coulter Epics Profile II flow cytometer.

EXAMPLE 11

Agglutination

Agglutinations were performed by adding 32 uL of the adsorbed diluted sera to a "V" bottom 96-well microtiter tray. Additional buffer K (13.5 uL) was added along with 4 uL of HLA-hydracytes. The reaction mixture was then thoroughly mixed. The agglutination wells were covered to prevent evaporation and the tray allowed to stand for 3 hours. For negative reactions, scored as "0", all hydracytes settled to the bottom of the wells and appeared as tight buttons. For positive reactions, scored "1" to "4", the buttons were more diffuse or nonexistent.

RESULTS

Hydracyte Preparations

Figure 2:
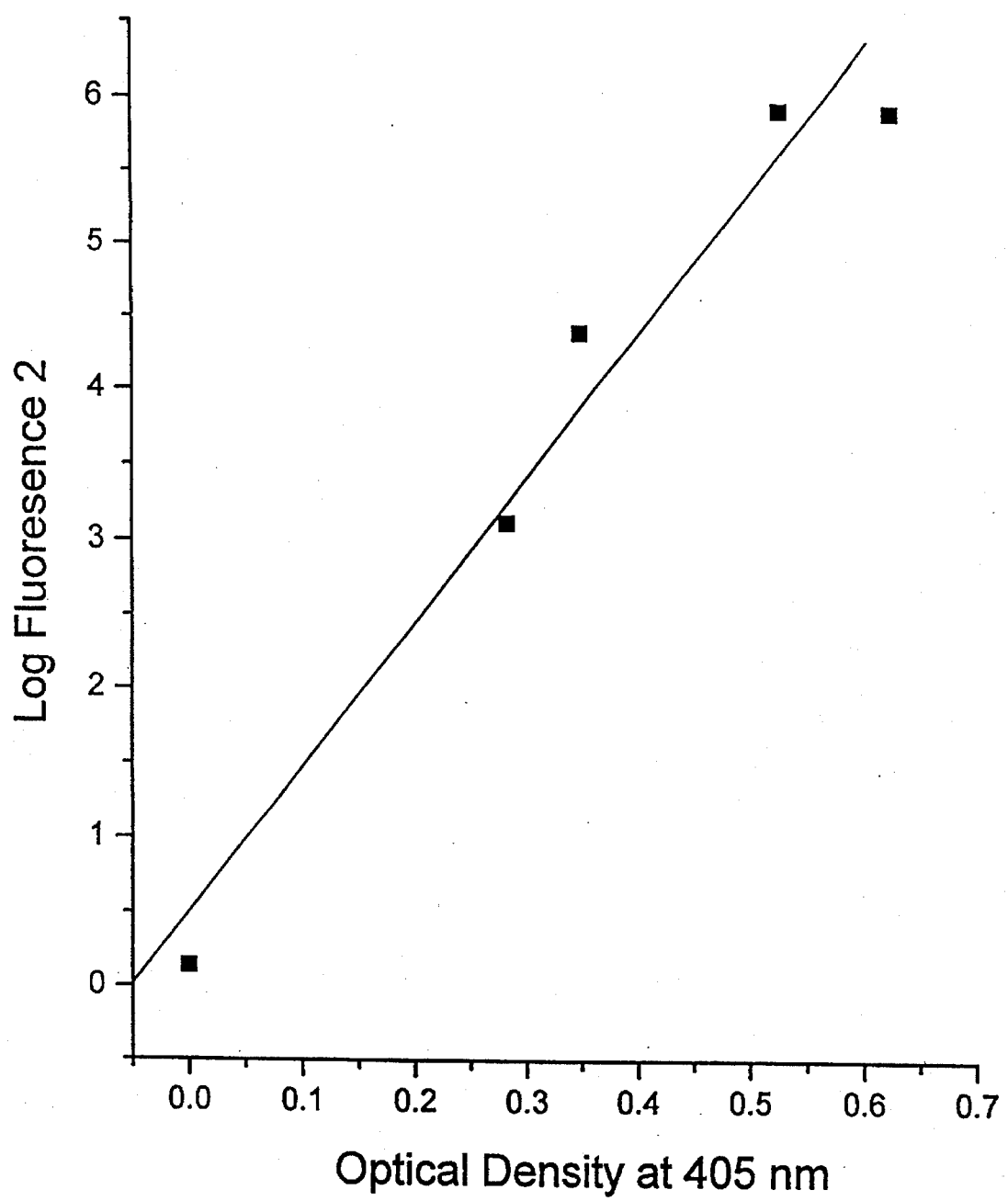
FIG. 2 is a graph showing correlation between the OD405 obtained from the Ellmans test (indirect measure of hydrazide formation) and the log fluorescence, LFL2, that is, a result of hydrazide formation.

Table I shows typical values for activation levels obtained for the preparation of hydracytes from duracytes. Each duracyte lot represents pooled sheep erythrocytes from different animal bleeds. The $OD_{405}$ values were obtained after reacting the duracytes (controls) and hydracytes with TBL and Ellmans reagent, as described. With regard to activation levels, good reproducibility was seen within and between lots of duracytes. Routinely, hydracytes were used with activation levels ranging between $1.24 \times 10^{11}$ and $3.2 \times 10^{11}$ groups per erythrocyte ($OD_{405}$ between 0.2 and 0.5). If necessary, higher levels of activation can be used; however, values approaching $6.2 \times 10^{11}$ or higher can lead to irreversible clumping of the cells. FIG. 1 shows the difference between the log orange fluorescence (LFL2) for duracytes (right) and hydracytes (left). Since there is a significant shift, LFL2 was used to monitor the activation reaction. FIG. 2 shows that a linear correlation exists between the optical density of activated duracytes, treated with TBL and Ellmans reagent, and the LFL2's of activated duracytes that were measured with the flow cytometer. A correlation coefficient of 0.980 was obtained from the data in FIG. 1.

TABLE I

Results from the Activation of Different Lots of Duracytes with Hydrazine

| Duracyte Lot # | Cell Type | OD405 | Delta OD405 | Activation Levels (X10 E-11) |
| --- | --- | --- | --- | --- |
| 42470-50 | Duracyte | 0.327 | — | — |
| 42470-97 | Hydracyte | 0.609 | 0.282 | 1.75 |
| 41182-49 | Duracyte | 0.400 | — | — |
| 43176-13 | Hydracyte | 0.743 | 0.343 | 2.13 |
| 39972-137 | Hydracyte | 0.764 | 0.364 | 2.26 |
| 42469-19 | Duracyte | 0.209 | — | — |
| 42469-31 | Hydracyte | 0.473 | 0.264 | 1.64 |

W6/32-Hydracytes

W6/32-hydracytes were analyzed by agglutination titers with goat anti-mouse antibody by flow cytometry. The typical value obtained for anti-mouse titers was 1/64,000 and 1/128,000. These titers correspond to detection levels of 15.6 to 7.8 ng/mL of anti-mouse, respectively.

Figure 3:
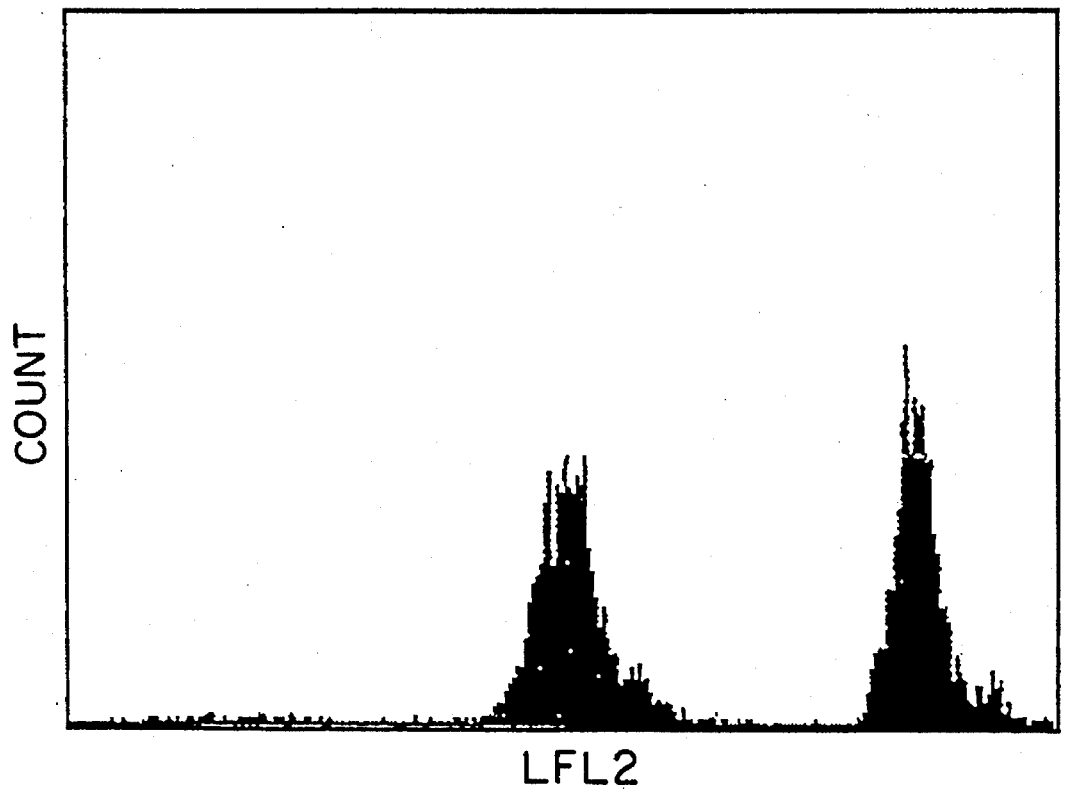
FIG. 3 is a graph showing log fluorescence shift obtained from binding of anti-mouse-PE to duracytes (left) and W6/32-hydracytes (right)
Figure 4:
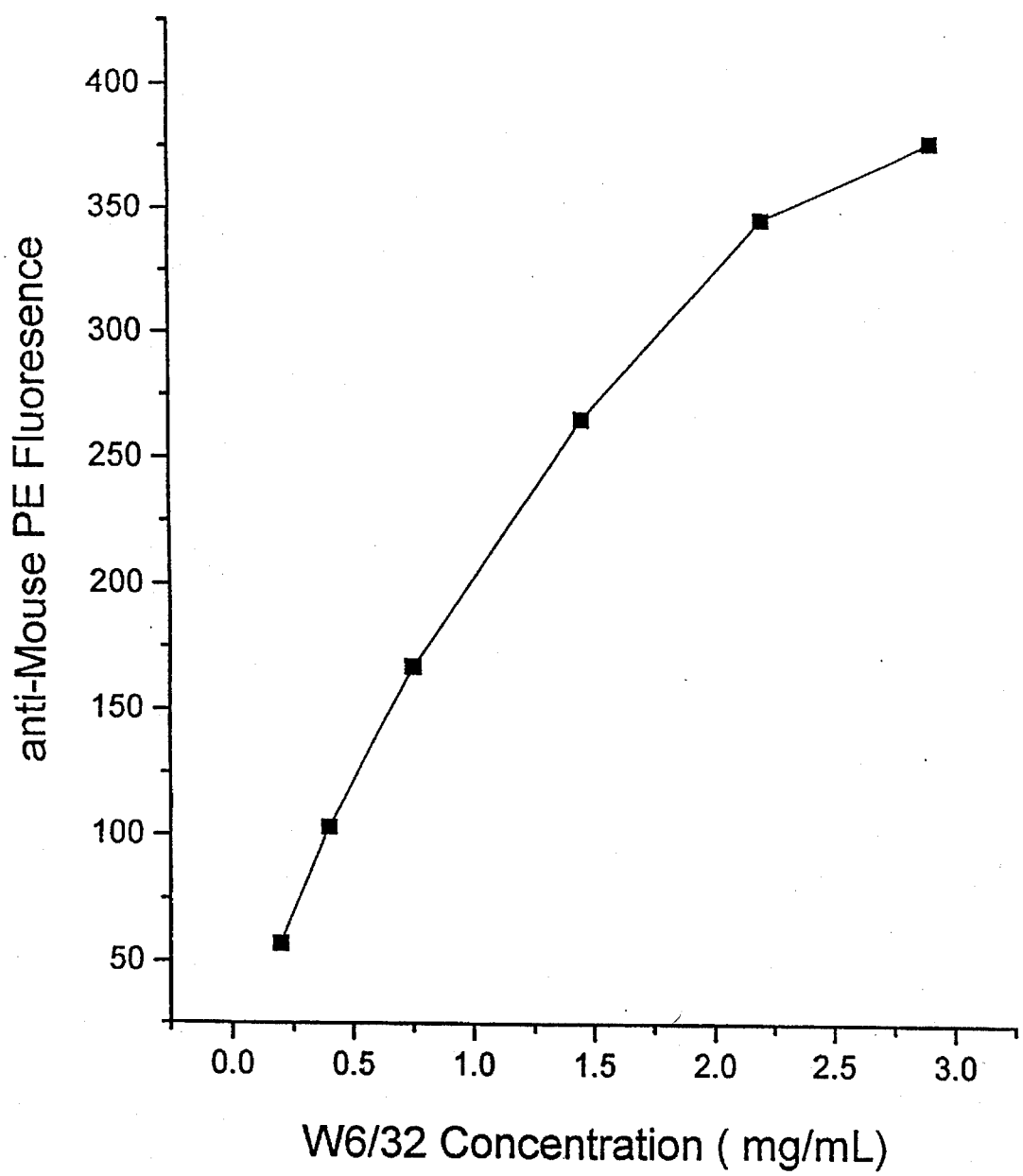
FIG. 4 is a graph showing fluorescence shifts obtained from binding anti-mouse-PE to W6/32-hydracytes that were prepared with various concentrations of W6/32.

The results of flow cytometry analysis are shown in FIGS. 3 and 4. FIG. 3 shows that the binding of anti-mouse-PE to W6/32-hydracytes results in a significant fluorescence shift relative to the binding of anti-mouse-PE to control hydracytes. With increasing concentration of W6/32 in the coupling reaction, the resulting fluorescence shift increases (FIG. 4). If hydracytes with activation levels lower than $1.24 \times 10^{11}$ are used, lower amounts of W6/32 are coupled.

HLA-Hydracytes

Figure 5:
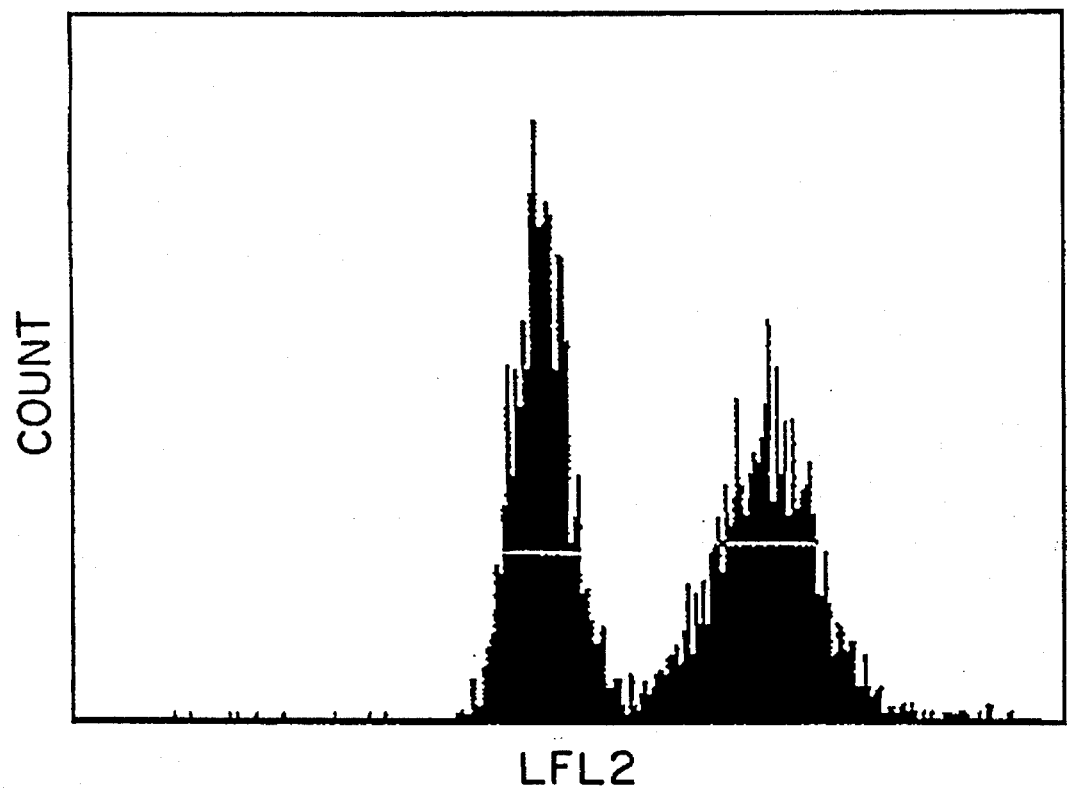
FIG. 5 is a graph showing log fluorescence shifts obtained from binding anti-B2M to W6/32-hydrazides (left) and HLA-hydracytes (right)
Figure 6:
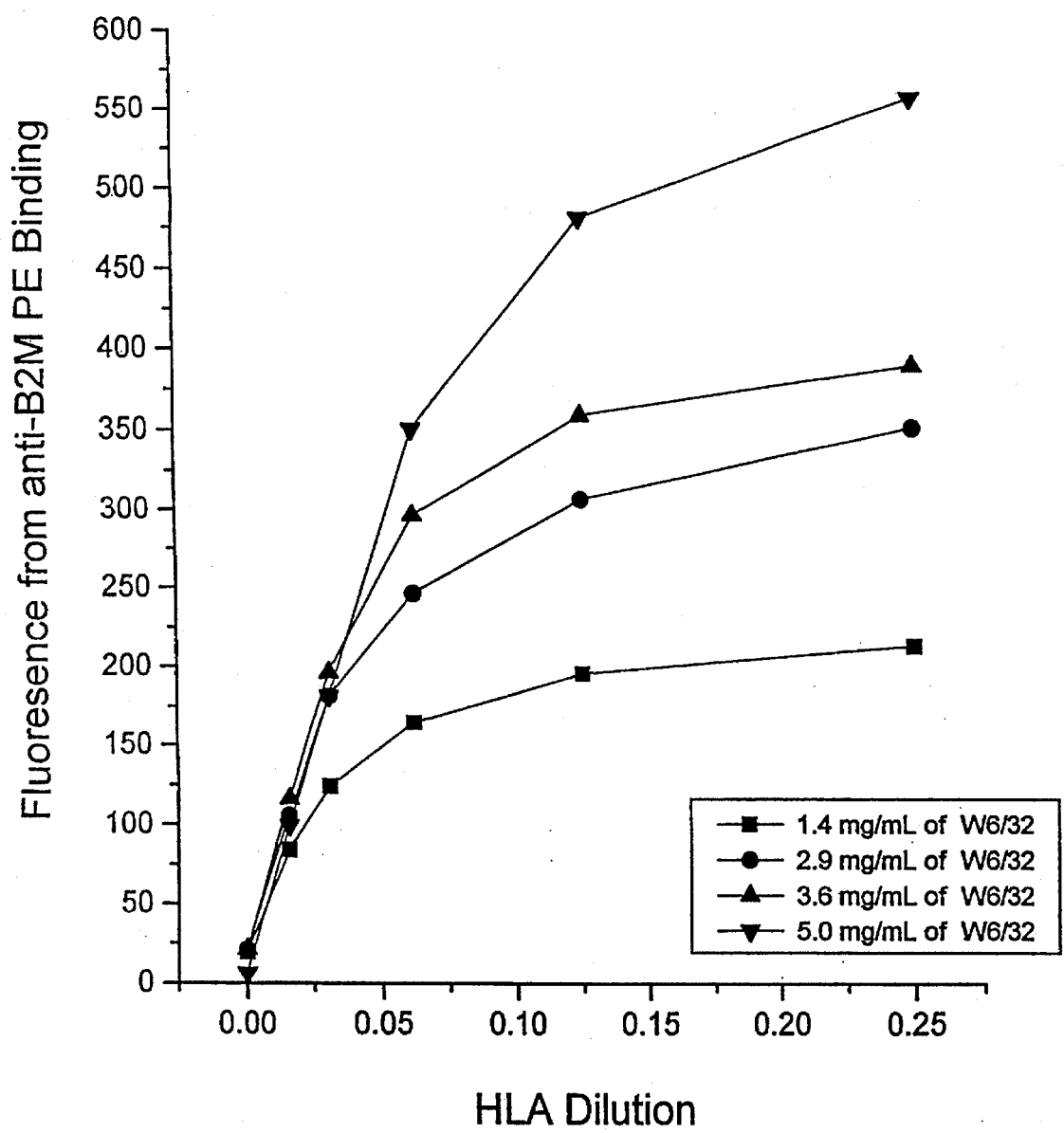
FIG. 6 is a graph showing fluorescence shifts obtained from the binding of anti-B2M-PE to various HLA-Hydracytes that were prepared with different HLA and W6/32 concentrations.

The binding of HLA to W6/32-hydracytes was followed by flow cytometry using anti-B2M-PE. FIG. 5 shows that the binding of anti-B2M-PE to an HLA-hydracyte results in a significant shift relative to the fluorescence obtained by the binding of anti-B2M-PE to W6/32-hydracytes. FIG. 6 shows that increasing the amount of HLA in the binding step increases the amount of HLA bound and that more HLA is bound to cells that have the greater amounts of W6/32 coupled to the hydracytes. It can also be seen that at the lowest concentration of W6/32 saturation, with HLA is taking place.

Serum Adsorptions

It was found that a majority of normal and allosera react with the W6/32-hydracytes routinely included as a control. These results are not surprising, since this type of reactivity of human serum to mouse IgG has been extensively reported in the literature and is currently referred to as HAMA (human anti-mouse antibodies). Since this reactivity is unacceptable, a few methods were evaluated to eliminate these interferences. It was found that the combined solid-liquid phase adsorption procedure, was satisfactory for eliminating this HAMA. The evaluation included 50 human sera samples from patients undergoing anti-OKT3 therapy. The HAMA ELISA titers of these samples were between 1/100 and 1/20,000. Using the solid-liquid phase adsorption, elimination of the human anti W6/32 interference, was achieved in 49 of the 50 samples. The one sample wherein the interference was not removed had the highest ELISA titer (1/10,000) of the samples obtained.

HLA-Induced Interferences

It was found that nearly all normal sera, even after solid-liquid phase adsorption, would show a positive agglutination when tested with HLA-hydracytes, but not with W6/32-hydracytes or W6/32-hydracytes bound with a Daudi (control) cell extract. Daudi does not produce Beta-2-microglobulin and does not have HLA (Class I) on its surface. The severity of the interference correlated with the amount of HLA bound. This phenomena is herein referred to as "HLA-Induced Interference". After trying numerous methods to eliminate these interferences, it was discovered that heating the HLA-hydracytes for 72 hours at 37° C. would eliminate these interferences. Interestingly, the amount of HLA bound to the cells did not appear to change due to the heat "curing" treatment (as determined by anti-B2M-PE binding (data not shown)).

HLA Hydracytes

Table II shows the identity and Class I HLA specificities of the various lymphocytes used. HLA was extracted from the corresponding lymphoblasts and then bound to W6/32- hydracytes to form the corresponding HLA-hydracytes. Also shown in Table II are the fluorescence shifts, FL2's, that were obtained when anti-B2M-PE was bound to each individual HLA-hydracyte. Since Class I HLA is composed of a unique heavy chain and common light chain (B2M), this measurement was used to indirectly quantitate the total HLA bound to each hydracyte.

TABLE II

HLA Specificities and Anti-B2M-PE Values for Various HLA-Hydracytes

| Cell ID # | Specificity | FL2 |
|---|---|---|
| 1 | A33,34; B58,72; Bw4,w6 | 351 |
| 2 | A3,31; B35,60; Bw6 | 419 |
| 3 | A1,3; B35,37; Bw4,w6 | 312 |
| 4 | A2,24; B8,50; Bw6 | 446 |
| 5 | A24,33; B56,65; Bw6 | 358 |
| 6 | A2,30; B55,60; Bw6 | 413 |
| 7 | A23,36; B53,58; Bw4 | 391 |
| 8 | A11,30; B13,52; Bw4 | 429 |
| 9 | A11,25; B27,44; Bw4 | 370 |
| 10 | A26,—; B13,55; Bw4,w6 | 404 |
| 11 | A3,28; B7,63; Bw4,w6 | 363 |
| 12 | A23,24; B7,49; Bw4,w6 | 360 |
| 13 | A1,24; B8,48; Bw6 | 422 |
| 14 | A26,28; B8,27; Bw4,w6 | 393 |
| 22 | A2,3; B47,51; Bw4 | 346 |
| 28 | A28,29; B13,35; Bw4,w6 | 335 |
| 30 | A1,33; B38,58; Bw4 | 349 |
| 31 | A23,74; B18,42; Bw6 | 405 |
| 502 | A2,25; B7; B38; Bw4,w6 | 411 |
| 503 | A1,32; B8,47; Bw4,w6 | 377 |
| 504 | A33,68; B14,48; Bw6 | 408 |
| 506 | A24,29; B7,54; Bw6 | 392 |

Blind Agglutination Study

In order to demonstrate that the assay was capable of distinguishing allosera from normal sera, a blind study in which 163 sera obtained from University Hospital in Leiden, Netherlands, were tested. A comparison of the CDC results obtained at Leiden compared to agglutination results obtained, is shown in Table III. Fifty-eight sera were shown to be positive in both the agglutination and CDC assays. Twenty-two sera were positive in the agglutination assay and negative in the CDC assay (false positives). Nine sera were negative in the agglutination assay and positive in the CDC assay (false negatives), and seventy-four sera were negative in both CDC and agglutination (true negatives). From the data in Table III, a chi square value of 63.97 was obtained with a $p<0.0001$. These results demonstrate that the assay can be used to effectively identify normal sera that are negative for HLA alloreactivity. Since in a typical sampling of multiparous sera only 10–20% of the samples would be CDC positive, this test provides a convenient means for significantly reducing the number of samples that would need to be tested by CDC.

The specificities obtained by CDC were compared with those obtained by agglutination. Of the 58 sera that were shown to be agglutination positive, clear specificities, by NIH CDC, were available for only 47 sera. A comparison of these 47 sera is shown in Table IV. A reasonable match was seen with 32 of the 47 sera (68%). The utilization of the assay described herein for the front end screening of multiparous sera has several advantages. These advantages include a constant source of antigens from lymphoblasts grown in culture, an assay that does not require complement, reagents that are reasonably stable at 4° C. to 8° C., an assay configuration and format that is amenable to automation, and the potential for eliminating false positives due to autoantibodies. Good stability at 4° C. to 8° C. has been observed. Utilizing additives that would allow for freezing the reagent at −20° C. to provide extended stability is considered possible.

Although the agglutination assay missed nine CDC positive sera, these sera were either nonspecific (possibly due to autoantibodies) or weak in CDC. The fact that alloreactivity was detected in 22 CDC negative sera suggests that the agglutination assay might be detecting CYNAP positive HLA alloantibodies that are otherwise missed by the standard no-wash CDC methodology.

TABLE III

Concordance Results for Agglutination vs CDC

| Results | Number of Sera |
|---|---|
| True Positives (+,+) | 56 |
| False Positives (+,−) | 22 |
| False Negatives (−,+) | 9 |
| True Negatives (−,−) | 74 |

TABLE IV

| Sera ID | Agglutination | CDC | Match |
|---|---|---|---|
| 1708 | 1,36 | 1+ | + |
| 2079 | 1,36+ | 8 | − |
| 299K | 2,17 | 2 | + |
| 178G | 2,17 | 2,28 | + |
| 97G | 2,28 | 2 | + |
| 236B | 9,Bw4 | 1 | − |
| 3104 | C7 | 25,17 | − |
| 1225 | NS | 2,7 | − |
| 168F | Bw6 | Bw6 | + |
| 226A | 2,28,9,10 | 2,28,22 | + |
| 191B | 2,16,17 | 2,57 | + |
| 282C | 7 | 7,40 | + |
| 272B | NS | 27 | − |
| 2338 | NS | Cw6,Cw7 | − |
| 2406 | 9 | 9 | + |
| 174C | 13 | 13 | + |
| 2259 | 8 | 8 | + |
| 194E | 5,35 | 5,35 | + |
| 1236 | NS | 35,Bw4 | − |
| 2619 | NS | 12,21 | − |
| 2002 | 2 | 2,28 | + |
| 2158 | 35,51,52 | 5,35 | + |
| 268G | 2,17 | 2,28 | + |
| 2024 | Bw4 | 5,35 | + |
| 309C | NS | 7,40,Cw2 | − |
| 269H | 7,22,40 | 7,40 | + |
| 2215 | 7,22 | 7 | + |
| 3047 | NS | 2,7 | − |
| 2035 | 9,Bw4 | 12 | − |
| 2327 | Multi | Bw4 | − |
| 237C | 2 | 2 | + |
| 1348 | 25,26 | 25, 17 | + |
| 147C | 2+ | 2 | + |
| 1258 | NS | 44 | − |
| 3148 | 17 | 17,11 | + |
| 308B | 13,15+ | 2,15,17 | + |
| 3137 | NS | 8 | − |
| 119B | Cw4 | Cw4 | + |
| 2204 | NS | 2,28 | − |
| 199J | 13,47,7 | 13,40 | + |
| 276F | 40,47,7 | Bw6 | + |
| 1247 | 35 | 35 | + |
| 188H | Bw6 | Bw6 | + |
| 186F | 9,Bw4 | 9,Bw4 | + |
| 618B | Bw6 | Bw6 | + |
| 208A | 7,47,22,42 | 7,27 | + |
| 2013 | 2,28 | 2,28 | + |

Numerous methods for coupling ligands to erythrocytes have been reported in the literature. None of these methods utilizes a site-directed method of coupling whereby the ligand (antibody) is immobilized through the carbohydrate portion of the Fc region. It has been suggested that this site directed coupling of antibody to solid-phase reagents is superior to random coupling procedures due to the proper orientation of the active site that is obtained with site-directed coupling. Site-directed coupling of antibodies to solid phases can be achieved by oxidation of the antibody (to produce aldehydes) and then coupling it to the solid phase having hydrazide groups available for reaction with the aldehyde groups of the antibody. The present invention has presented methodology to activate red blood cells (duracytes) and has shown that it can be utilized to couple active W6/32 to activated duracytes (hydracytes) which, in turn, can bind HLA and then detect HLA allosera.

Methods are presented by the invention for quantitating hydrazide groups that are on solid phases or cells. It has now been shown that TBL, which reacts more rapidly and to a much greater extent with hydrazides than with amines at pH 5.0, can be used to convert hydrazides to sulfhydryls which, in turn, can be quantitated with Ellmans reagent. This provides an indirect method for quantitating the hydrazides prepared on the stabilized cells.

In addition to the Ellmans quantitation, a measurement of the cells of the LFL2 using a flow cytometer is a very convenient method for following the actual progression of hydrazide derivatization of the cells in a stat method. This is very convenient and helpful since the rate of hydrazide derivatization can vary with reaction vessel size, stir rate, temperature and pH.

While the present invention has been particularly demonstrated with reference to specific materials and examples, it will be understood by those skilled in the art that changes in form and details can be made therein without departing from the spirit and scope of the invention, as defined by the following claims.

We claim:

1. A method for quantitating the number of hydrazide groups that are on solid particles, semisolid particles or cells wherein said hydrazide groups are formed on said solid particles, semisolid particles or cells by reacting carboxylic acid groups located on the surface molecules of said solid particles, semisolid particles or cells with hydrazine groups in the presence of 1-ethyl-3-(3-dimethylaminopropyl)carbodiimide hydrochloride, which quantitation method comprises reacting thiobutyrolactone with said hydrazide groups at a pH of about 5.0 to selectively convert said hydrazide groups to sulfhydryl groups, and adding 5,5'-dithio-bis(2-nitrobenzoic acid) to said sulfhydryl groups; whereby intensity of color development due to said 5,5-dithio-bis(2-nitrobenzoic acid) is correlated, based upon standards correlating color intensity to sulhydryl group quantity, with the quantity of sulfhydryl groups, and consequently the quantity of hydrazide groups, present on said solid particles, semisolid particles or cells.

2. A method for approximating the number of hydrazide groups that are on cells, wherein said hydrazide groups are formed on said cells by reacting carboxylic acid groups located on the surface molecules of said cells with hydrazine groups in the presence of 1-ethyl-3-(3-dimethylaminopropyl)carbodiimide hydrochloride which method comprises measuring fluorescence of said cells using flow cytometry and comparing said measurement to standards correlating fluorescence with hydrazide group quantity incorporated into cell surface molecules, said comparison yielding approximately the number of hydrazide groups on said cells.

* * * * *

UNITED STATES PATENT AND TRADEMARK OFFICE
CERTIFICATE OF CORRECTION

PATENT NO. : 5,591,598
DATED : January 7, 1997
INVENTOR(S) : Granados, et. al.

It is certified that error appears in the above-indentified patent and that said Letters Patent is hereby corrected as shown below:

Column 14, line 22, change "groups," to --groups--.

Signed and Sealed this

Twenty-ninth Day of July, 1997

Attest:

BRUCE LEHMAN

Attesting Officer

Commissioner of Patents and Trademarks